United States Patent
Young et al.

(10) Patent No.: US 8,409,412 B2
(45) Date of Patent: Apr. 2, 2013

(54) ENZYMATIC REAGENT INKS FOR USE IN TEST STRIPS HAVING A PREDETERMINED CALIBRATION CODE

(75) Inventors: Gary Young, Inverness (GB); Michael O'Connell, Muir of Ord (GB); Ian McArthur, Inverness (GB); Alan McNeilage, Inverness (GB); Nick Phippen, Inverness (GB); Manuel Alvarez-Icaza, Inverness (GB)

(73) Assignee: LifeScan Scotland, Ltd., Inverness (GB)

( * ) Notice: Subject to any disclaimer, the term of this patent is extended or adjusted under 35 U.S.C. 154(b) by 320 days.

(21) Appl. No.: 12/861,822

(22) Filed: Aug. 23, 2010

(65) Prior Publication Data

US 2012/0043204 A1    Feb. 23, 2012

(51) Int. Cl.
*G01N 27/327* (2006.01)

(52) U.S. Cl. ................ 204/403.04; 205/777.5

(58) Field of Classification Search ............. 204/403.01, 204/403.04; 205/777.5, 792; 600/347
See application file for complete search history.

(56) References Cited

U.S. PATENT DOCUMENTS

| | | | |
|---|---|---|---|
| 5,708,247 A | 1/1998 | McAleer et al. | |
| 5,951,836 A | 9/1999 | McAleer et al. | |
| 6,241,862 B1 | 6/2001 | McAleer et al. | |
| 6,284,125 B1 | 9/2001 | Hodges et al. | |
| 7,112,265 B1 | 9/2006 | McAleer et al. | |
| 7,462,265 B2 | 12/2008 | Leach et al. | |
| 2007/0045126 A1 | 3/2007 | Beer et al. | |
| 2009/0208743 A1 | 8/2009 | Pettit | |
| 2010/0112612 A1 | 5/2010 | Dilleen et al. | |
| 2010/0112678 A1 | 5/2010 | Dilleen et al. | |

FOREIGN PATENT DOCUMENTS

| | | |
|---|---|---|
| EP | 1916309 A2 | 4/2008 |
| EP | 2243840 A1 | 10/2010 |
| WO | WO 97/30344 A1 | 8/1997 |
| WO | WO 03/014378 A2 | 2/2003 |
| WO | WO 03/091717 A1 | 11/2003 |
| WO | WO 2006/096619 A1 | 9/2006 |

OTHER PUBLICATIONS

Industrial Minerals and Their Uses, 1996, p. 591, Peter Ciullo.*
Laurinavicius. V, et al., "Oxygen Insensitive Glucose Biosensor Based on PQQ-Dependent Glucose Dehydrogenase" Analytical Letters, Taylor & Francis Inc., U.S., vol. 32, No. 2, Jan. 1, 1999 pp. 299-316, XP009070271, ISSN: 0003-2719, DOI: 10. 1080/00032719908542822.
International PCT Search Report, PCT Application No. PCT/GB2011/001245, dated Oct. 28, 2011, 4 pages European Patent Office, Rijswijk, Netherlands.

* cited by examiner

*Primary Examiner* — Kaj K Olsen

(57) ABSTRACT

The invention provides an enzyme ink useful in test strips that provides a test strip bias, at the low and high glucose ends, falling within a desired target range. The ink of the invention permits an improved method for the production of single calibration code strip lots with good yields.

12 Claims, 6 Drawing Sheets

ENZYMATIC REAGENT INKS FOR USE IN TEST STRIPS HAVING A PREDETERMINED CALIBRATION CODE

FIELD OF THE INVENTION

The invention relates to enzymatic reagent inks, or enzyme inks, useful in electrochemical test strips. In particular, the invention relates to reagent inks for use in electrochemical test strips having a predetermined calibration code.

BACKGROUND OF THE INVENTION

Electrochemical test strips are designed to measure the concentration of an analyte, such as glucose, in a body fluid sample. In the case of the measurement of glucose in a blood sample, the glucose measurement is based on the selective oxidation of glucose, as for example, by the glucose oxidase enzyme. The glucose is oxidized to gluconic acid by the oxidized form of glucose oxidase and the oxidized enzyme is converted to its reduced state. Next, the reduced enzyme is re-oxidized by reaction with a mediator, such as ferricyanide. During this re-oxidation, the ferricyanide mediator is reduced to ferrocyanide.

When these reactions are conducted with a test voltage applied between two electrodes, a test current is created by the electrochemical re-oxidation of the reduced mediator at the electrode surface. Since, in an ideal environment, the amount of reduced mediator created during the chemical reaction is directly proportional to the amount of glucose in the sample positioned between the electrodes, the test current generated is proportional to the glucose content of the sample.

Test meters that use this principle enable an individual to sample and test a blood sample and determine the blood's glucose concentration at any given time. The glucose current generated is detected by the test meter and converted into a glucose concentration reading using an algorithm that relates the test current to a glucose concentration via a simple mathematical formula. In general, the test meters work in conjunction with a disposable test strip that may include a sample-receiving chamber and at least two electrodes disposed within the sample-receiving chamber in addition to the enzyme and the mediator.

Such a glucose test using a test meter and strip use batch calibration information about the test strip, such as batch slope and intercept values, determined from the manufacturing of a particular strip lot, or batch. When a user performs a glucose test using a strip from a particular strip lot, the batch slope and batch intercept information must be inputted into a test meter in the form of a calibration code by the user if the information varies batch-to-batch. If a user forgets to account for a change in calibration factors when using a different lot of test strips, there is a possibility that an inaccurate glucose measurement result may occur. Such an error can lead to insulin dose errors by the individual resulting in a hypo- or hyperglycemic episode.

To overcome this disadvantage of using test strips, test strip manufacturers have developed test strips and methods of manufacturing the strips, in which test strip lots can be prepared that do not require a user to input any calibration information before performing a test measurement because a high percentage of test strip lots can be produced that have a relatively constant batch slope and batch intercept. Thus, the test strip lots effectively have the same calibration and, when the test strips are used in a glucose test meter manufactured with the calibration information, no calibration coding is necessary or required of the user during each usage of the test strips.

DETAILED DESCRIPTION OF THE INVENTION

Figure 1A:
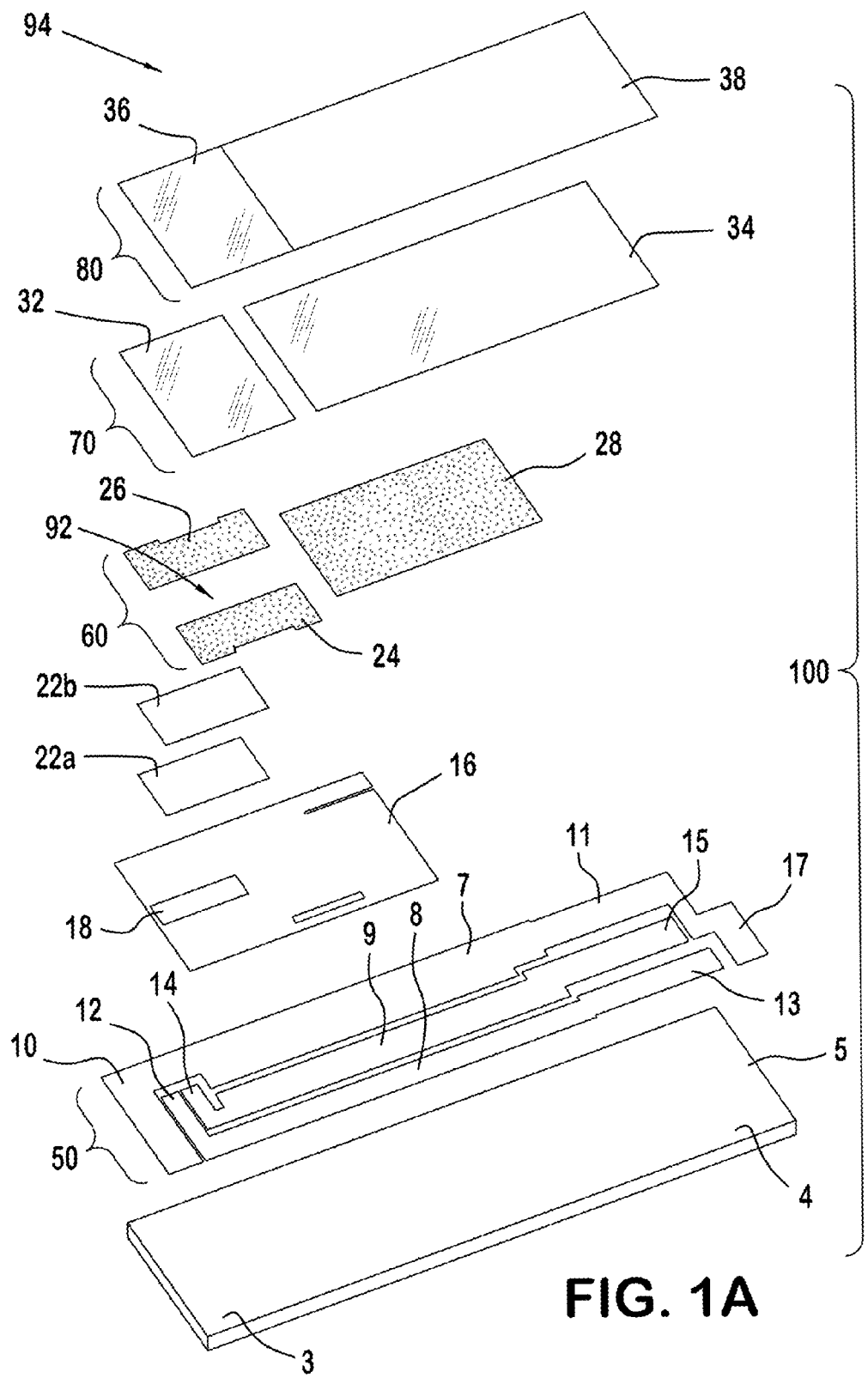
FIG. 1A is an exploded, perspective view of a test strip.

It is a discovery of the invention that bias, in response to high and low glucose levels, of a test strip lot may be impacted by the selection of fumed silicas used in the strips' enzyme ink. More specifically, it is a discovery of the invention that the use of at least two fumed silicas, one with a greater surface area and carbon content than the other, in the enzyme ink of the test strips provides a test strip bias at the low and high glucose ends that falls within a desired target range thus providing an improved method for the production of single calibration code strip lots with good yields. In one embodiment, the test strips from the process have bias values that fall within predetermined target ranges, for example, within predetermined target ranges.

In one embodiment the invention provides an enzyme ink composition comprising, consisting essentially of an enzyme capable of selectively recognizing glucose in a blood sample, a mediator, and one or more materials capable of regulating the mass transport of the mediator so that biases in response to one or more of a low glucose value and a high glucose value falls within a predetermined target for a predetermined calibration code.

The invention may find its greatest utility in enzyme inks for use in electrochemical-based test strips for the determination of glucose levels in whole blood samples. More preferably, the enzyme inks of the invention are used in electrochemical test strips for measuring glucose, which electrodes have co-planar electrodes. Most preferably the inks of the invention are used in ULTRA™ type test strips as disclosed in U.S. Pat. Nos. 5,708,247, 5,95,836, 7,112,265, 6241,862, 6284,125, 7,462,265 and U.S. Patent Publication Nos. 20100112678 and 20100112612, incorporated herein in their entireties by reference.

The inks of the invention preferably contain at least two hydrophobic, fumed silica materials that are chemically equivalent, meaning that the materials have equal stability and are composed of substantially the same materials, but differ in BET measured surface area and total carbon content. By "BET measured surface area" is meant the BET surface area of hydrophilic silica.

The fumed silicas useful in the invention may be any such silica capable of providing the desired bias response at high and low glucose levels. It is believed that this can be accomplished by using materials that regulate the mass transport of the mediator thereby maintaining counter/reference electrode function throughout the test time. Fumed silicas useful in the invention are commercially available or may be produced by known methods such as by burning silicon tetrachloride in an oxygen-hydrogen flame or from the vaporization of quartz sand in an electric arc. Suitable silicas include, without limitation those under the trade names HDK® available from Wacker Chemie GmbH, CAB-O-SIL® available from Cabot and AEROSIL® available from Evonik deGussa Ltd. Preferably, the fumed silicas used are HDK silicas.

One ordinarily skilled in the art will recognize that any material that is water-soluble, inert and that can modify the mass transport of the mediator in the solvating reagent pad of the test strip can be used in lieu of the fumed silicas. However, the silicas may provide the best material in that one silica typically is used in the reagent and can be easily blended with a second silica.

In a preferred embodiment, one silica material with a BET measured surface area of about 130 to 170 $m^2/g$ and carbon content of about 0.8 to 1.2 weight percent is combined with a second silica material that has a BET measured surface area of about 270 to 330 $m^2/g$ and a carbon content of about 1.4 to 2.6 weight percent. For purposes of the invention, the surface area is calculated using the BET theory for physical adsorption of gas molecules on a solid surface according to test procedure DIN ISO 9277/DIN 66132. Preferably, the fumed silicas used are HDK silicas and most preferably are a combination of HDK H15 and HDK H30 silicas.

The amount of each of the silicas useful in the invention is an amount effective to provide the desired degree of bias response at one or both of high and low glucose levels. Typically, the amount of the lower surface area and lower carbon content fumed silica, such as HDK H15, will be about 99 to about 1, preferably 75 to about 45 and more preferably about 71 to about 68 weight percent of the total amount of fumed silica used in the enzyme ink. The amount of the greater surface area and higher carbon content silica, such as HDK 30, will be about 1 to about 99, preferably 25 to about 55, and more preferably about 29 to about 32 weight percent.

The fumed silicas may be combined with a suitable enzyme and mediator to form the enzyme reagent ink. Useful enzymes are any enzyme that is capable of selectively recognizing glucose within a blood sample and preferably is a redox enzyme including, without limitation, glucose oxidase or glucose dehydrogenase. The glucose dehydrogenase may have a pyrrolo-quinoline quinine co-factor or a flavin adenine dinucleotide co-factor. More preferably, the enzyme is glucose oxidase. Suitable mediators include without limitation, ferricyanide, ruthenium hexamine trichloride, or the like. Preferably, the mediator is potassium ferricyanide. Additional components of the enzyme ink may be, without limitation, a buffer, an adhesion promoter, preferably polyvinyl alcohol ("PVA"), a film-forming agent, preferably polyvinyl pyrrolidone-vinyl acetate, an antifoam compound, a gelling and thickening agent, preferably hydroxyethyl cellulose ("HEC"), water, preferably Analar grade, and combinations thereof.

A most preferred formulation of the enzyme ink of the invention is: about 0.3 percent by mass of an antifoam compound; about 0.6 percent by mass PVA; about 0.6 percent by mass citric acid; about 1.9 percent by mass trisodium citrate; about 0.6 percent by mass polyvinylpyrrolidone-vinyl acetate copolymer; about 3.27 percent by mass hydroxyethyl cellulose; about 3.6 percent by mass of fumed silica with a BET measured surface area of about 130 to 170 $m^2/g$ and carbon content of about 0.8 to 1.2 weight %; about 1.3 percent by mass of a fumed silica that has a BET measured surface area of about 270 to about 330 and a carbon content of about 1.2 to 2.6 weight %; about 0.03 percent by mass of potassium hexacyanoferrate III; about 23 percent by mass of potassium ferricyanide; about 2.1 percent by mass of glucose oxidase and about 62.4 percent by mass Analar grade water. The enzymatic reagent ink of the invention may be made by any convenient process.

The bias of the strips of the invention may be calibrated by any convenient method including without limitation, the following method. An amount, typically around 1500 strips, are selected at random from the batch. Blood from 12 different donors is spiked to each of six levels of glucose and eight strips are given blood from identical donors and levels so that a total of 12×6×8=576 tests are conducted for that batch. These are benchmarked against actual blood glucose concentration by measuring these using a standard laboratory analyzer such as Yellow Springs Instrument ("YSI"). A graph of measured glucose concentration is plotted against actual glucose concentration (or measured current versus YSI current), and a formula y=mx+c least squares fitted to the graph to give a value for batch slope m and batch intercept c for the remaining strips from the lot or batch. The difference in response to high and low blood glucose contents may be described by any method that measures bias change over an operational range. For example, the linearity may be described by the term a in the quadratic calibration $ax^2+mx+c$, wherein m is the slope and c is the slope intercept. Another convenient measure is the linearity metric Delta 150 which is defined as the difference between the percent bias at 500 mg/dl glucose and at 150 mg/dl and may be represented by the following equation:

$$\text{Delta\_150} = \% \text{ bias}_{500\ mg/dl} - \% \text{ bias}_{150\ mg/dl}$$

The amount of the fumed silicas in the enzyme ink can be used to affect the potassium ferricyanide diffusion of the strip and, thus, alter the counter electrode-reference electrode efficiency. This can be used to alter the bias at one or both of high and low glucose levels. After the amount of fumed silicas is set, a verification run may be performed to verify that a linearity substantially equal to the target values is achieved. If the linearity is substantially equal to the target values, then the methods will move forward to large-scale production batches. However, if the second linearity is not substantially equal to the target range, then the ratio of the fumed silicas used is adjusted and more strips prepared and tested to verify that the modified amounts provide the bias that is desired. This can be repeated as necessary It should be noted that other factors including, without limitation, the amount of mediator, the conductive ink lot, oxidized mediator lot, mixing time, mixing process, standing time, preconditioning of substrate, mesh type, mesh deformability, working electrode length, working electrode area, working electrode separation and snap distance, may affect one or both of the batch slope and intercept. These can be controlled so as to be sufficiently identical during each run such that a substantially constant slope and intercept are obtained batch-to-batch. Preferably, the working electrode area and the amount of reduced mediator are controlled, as described in United States Patent Publication No. 20090208743A1 incorporated herein in its entirety by reference, so as to achieve a substantially constant slope and intercept.

A test strip using the enzyme ink of the invention may be manufactured using any convenient, known method including, without limitation, web printing, screen printing and combinations thereof. For example, the strip may be manufactured by sequential, aligned formation of a patterned conductor layer, insulation layer, reagent layer, patterned adhesive layer, hydrophilic layer and a top film onto an electrically insulating substrate.

An exemplary web printing process is as follows. A substrate is used that may be nylon, polycarbonate, polyimide, polyvinyl chloride, polyethylene, polypropylene, glycolated polyester, polyester and combinations thereof. Preferably, the substrate is a polyester, more preferably Melinex ST328, which is manufactured by DuPont Teijin Films. Prior to entering one or more printing stations, the substrate may be preconditioned to reduce the amount of expansion and stretch that can occur in the strip manufacturing process. In the preconditioning step, the substrate may be heated to a temperature, which is not exceeded in the subsequent print steps. For example, the substrate may be heated to approximately 160° C. Generally, the heating takes place under tension of between about 150N and 180N more typically around 165N. Alternatively, preconditioning the substrate can be heated to a temperature sufficient to remove the irreversible stretch, again optionally while under tension as described above.

Preferably, the substrate is held under a tension of approximately 165N throughout the process in order to maintain registration of the layers to be printed. The substrate is also subjected to various temperatures of about 140° C. or less in order to dry the printed inks during each printing step. Optionally, prior to printing a cleaning system may be used which cleans the top, or print, side and the underside of the substrate using a vacuum and brush system.

One or more prints with carbon with metallic particles, silver/silver chloride ink or gold or palladium based inks or any combination thereof in one or more printing steps may be used to provide an electrode layer. In one embodiment, prior to the printing process and immediately after drying, the substrate is passed over a first chilled roller, to rapidly cool the substrate to a predetermined temperature, typically room temperature around 18-21° C. and typically 19.5° C.+/−0.5° C. After the printed carbon patterns are deposited in the printing process, the substrate may be passed over a second chilled roller.

Any ink suitable for use as an insulation ink and applicable in a print station in a web manufacturing process may be used including, without limitation, Ercon E6110-116 Jet Black Insulayer Ink, which may be purchased from Ercon, Inc. Immediately after drying, the substrate, including printed carbon and insulation patterns, is passed over third chilled roller as described above.

A first enzyme ink printing may then take place using an ink of the invention. After the first enzyme ink printing process and immediately after drying, the substrate, including printed carbon and insulation patterns, is passed over a fourth chilled roller. One or more of a topside, underside and side humidification may be provided. For example, an arrangement of pipes may provide a substantially constant stream of humidified air above, below and sideways onto the substrate and layers ensuring the water content of the ink is maintained at a constant level. The amount and arrangement of humidification, typically pipes carrying humidified air, will depend, amongst other things, upon the amount of humidification required, the water content of the ink, the humidity and temperature of the surrounding air, the temperature of the substrate as it approaches the enzyme print station, the temperature of the print roller, the size of the screen and the exposure of the screen to the surrounding, unhumidified air.

Figure 1B:
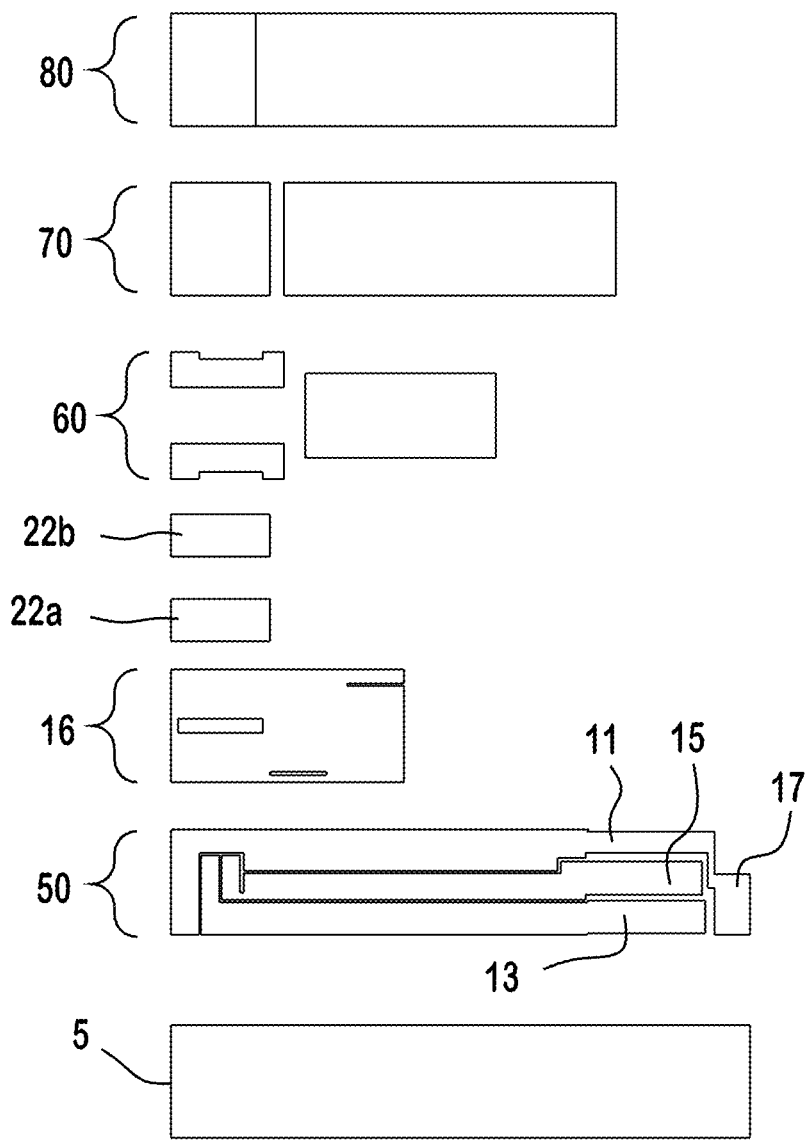
FIG. 1B is a top plan view of the strip of FIG. 1A.

FIG. 1A is an exploded perspective view of an exemplary test strip 100, which may include seven layers disposed on a substrate 5. FIG. 1B is an exemplary top plan view of the individual layers of FIG. 1A. The seven layers disposed on substrate 5 can be a conductive layer 50, which can also be referred to as electrode layer 50, an insulation layer 16, two overlapping reagent layers 22a and 22b, an adhesive layer 60, a hydrophilic layer 70, and a top layer 80.

Figure 1C:
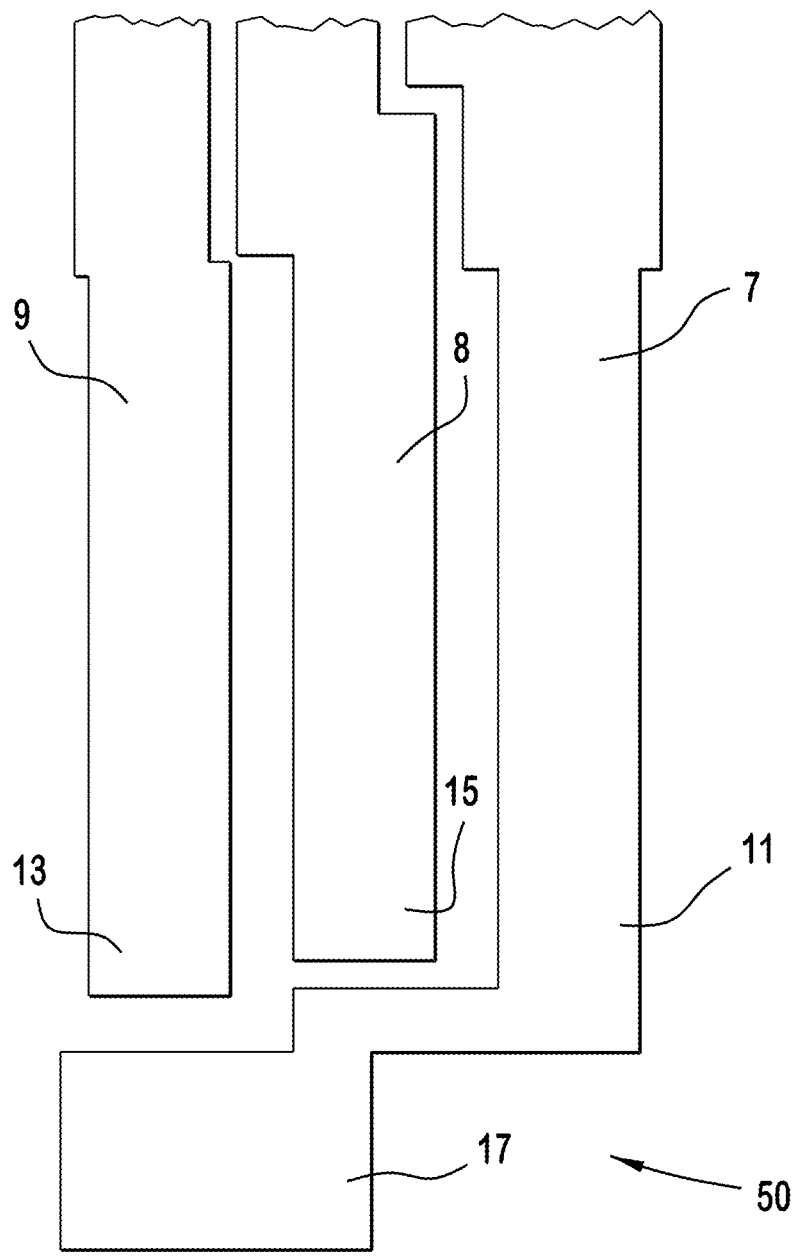
FIG. 1C is a magnified view of a portion of the test Strip of FIG. 1A.

For test strip 100, as illustrated in FIGS. 1A, 1B and 1C, conductive layer 50 may include a reference electrode 10, a first working electrode 12, a second working electrode 14, a first contact pad 13, a second contact pad 15, a reference contact pad 11, a first working electrode track 8, a second working electrode track 9, a reference electrode track 7, and a strip detection bar 17. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. A test meter can detect that test strip 100 has been properly inserted by measuring a continuity between reference contact pad 11 and strip detection bar 17, as illustrated in FIGS. 1A, 1B and 1C.

The enzyme ink layer may be disposed on a portion of the conductive layer 50, substrate 5, and insulation layer 16 as illustrated in FIGS. 1A and 1B. In one embodiment, two successive enzyme ink layers 22a and 22b may be screen-printed on conductive layer 50, typically also overlapping slightly insulation layer 16. For test strip 100, adhesive layer 60 may include first adhesive pad 24, second adhesive pad 26, and third adhesive pad 28, as illustrated in FIGS. 8A to 8F and 9. Adhesive layer 60 can be deposited on test strip 100 after the deposition of reagent layer 22. First adhesive pad 24 and second adhesive pad 26 can be aligned to be immediately adjacent to, touch, or partially overlap with reagent layer 22. Adhesive layer 60 may include a water based acrylic copolymer pressure sensitive adhesive which is commercially available from Tape Specialties LTD, which is located in Tring, Herts, United Kingdom (part #A6435). Adhesive layer 60 is disposed on a portion of insulation layer 16, conductive layer 50, and substrate 5. Adhesive layer 60 binds hydrophilic layer 70 to test strip 100.

Hydrophilic layer 70 may include a distal hydrophilic portion 32 and proximal hydrophilic portion 34, as illustrated in FIGS. 8A and 8B. Hydrophilic layer 70 may be a polyester having one hydrophilic surface such as an anti-fog coating, which is commercially available from 3M.

The final layer to be added to test strip 100 is top layer 80, as illustrated in FIGS. 1A and 1B. Top layer 80 may include a clear portion 36 and opaque portion 38, as illustrated in FIGS. 1A and 1B. Top layer 80 is disposed on and adhered to hydrophilic layer 70. Top layer 80 may be a polyester that has an adhesive coating on one side. It should be noted that the clear portion 36 substantially overlaps distal hydrophilic portion 32, which allows a user to visually confirm that the sample-receiving chamber 92 may be sufficiently filled. Opaque portion 38 helps the user observe a high degree of contrast between a colored fluid such as, for example, blood within the sample-receiving chamber 92 and the opaque portion 38.

The invention will be further clarified by a consideration of the following, non-limiting examples.

EXAMPLES

Example 1

The following procedure was employed to prepare an exemplary enzymatic ink of the invention.

A PVA-antifoam-citric acid solution was prepared by combining 0.5 ml of DC 1500 Antifoam (commercially available from BDH/Merek Ltd.) with 7500 grams of water (AnalaR, available from BDH/Merck Ltd.). Next, 90 grams of PVA (Sigma-Aldrich, MW 85,000-124,000, 87%-89% hydrolyzed) were added to the solution and homogenized at >7000 RPM for 2 hours. After homogenization, 81.5 grams of citric acid were mixed into the solution.

A pH adjusting solution was prepared by mixing 270 grams of trisodium citrate into 1000 ml of water. The pH of the PVA-antifoam-citric acid solution was then adjusted to pH 5 by adding a sufficient amount of trisodium citrate solution.

The pH 5 solution was filtered through a 125 micron sieve and transferred to a 30 liter stainless steel pot. Additional water was added to the 30 liter steel pot until the total solution weight was 9250 grams. 44.5 mL of DC 1500 Antifoam were then added to the stainless steel pot.

A 90 mm diameter mixer blade was attached to a Dispersmat mixer and mounted to the stainless steel pot such that the mixer blade was 2 centimeters above the bottom of the pot. The mixer was set at 800 RPM and then 90 grams of polyvinylpyrrolidone-vinyl acetate (PVP/VA S-630 co-polymer, commercially available from the ISP Company, and which has a 60/40 ratio and a molecular weight of 24,000 to 30,000) and 449 grams of HEC (commercially available as Natrosol 250G) were added during first two minutes of mixing. Next, the mixing speed was increased to 5500 RPMs and continued for five additional minutes, resulting in a HEC solution.

After the mixing period, the HEC solution was transferred to a 15 liter keg and mixed gently (i.e., rolled) for 12 to 25 hours. The viscosity was then measured and confirmed to be within the range of 13,000 to 17,000 cP (measured at 25° C. and 5 RPMs).

The rolled HEC solution was equilibrated to between 7° C. and 10° C. Next, 9000 grams of the rolled and equilibrated HEC solution were mixed with 446 grams of hydrophobic silica material H15 and 209 g of hydrophobic silica material H30 (Wacker HDK grade, commercially available from Wacker Chemie AG) in a 30 liter stainless steel pot to form an HEC/silica mixture.

A 175 mm diameter mixer blade was attached to the Dispersmat mixer and mounted to the stainless steel pot so that the mixer blade was at the bottom of the pot. The combined HEC/silica mixture was mixed at 2600 RPM for 16 minutes. The density of the formulation was then measured (using a Cole-Parmer Pycnometer) to determined to be in the range of from about 0.9650-1.0150 g/cm$^3$ g/cm$^3$.

The HEC-silica mixture was then transferred to a 15 liter keg and rolled gently for 8 to 16 hours. The viscosity was then measured and confirmed to be within 37,000 to 50,000 cP (measured at 25° C. and 10 RPMs).

4515 grams of HEC-silica mixture were combined with 1386 grams of potassium ferricyanide, 1.6 g potassium hexacyanoferrate III, and 126 grams of glucose oxidase in a 15 liter stainless steel pot. A 125 mm diameter mixer blade was attached to the Dispersmat mixer and mounted to the stainless steel pot so that the mixer blade was at the bottom of the pot and the mixture mixed at 1500 RPMs for 15 minutes. After mixing, the pH was in the range from about 4.8 to 5.4 and the viscosity was in the range from about 36,000 to 48,000 cP (measured at 25° C. and 10 RPM).

Examples 2 through 6

The method of Example 1 was used to prepare enzyme inks except that the amounts of fumed silicas used were as set forth in Table 1 below.

TABLE 1

| Example | % H30 Surface Area Carbon Content | % H15 Surface Area Carbon Content | Mixture Surface Area Carbon Content |
|---|---|---|---|
| 2 | 0% 300 m$^2$/g 2 | 100% 150 m$^2$/g 1 | — 150 m$^2$/g 1 |
| 3 | 100% 300 m$^2$/g 2 | 0% 150 m$^2$/g 1 | — 300 m$^2$/g 2 |
| 4 | 20% 300 m$^2$/g 2 | 80% 150 m$^2$/g 1 | — 180 m$^2$/g 1.2 |
| 5 | 50% 300 m$^2$/g 2 | 50% 150 m$^2$/g 1 | — 225 m$^2$/g 1.5 |
| 6 | 80% 300 m$^2$/g 2 | 20% 150 m$^2$/g 1 | — 270 m$^2$/g 1.8 |

Figure 2:
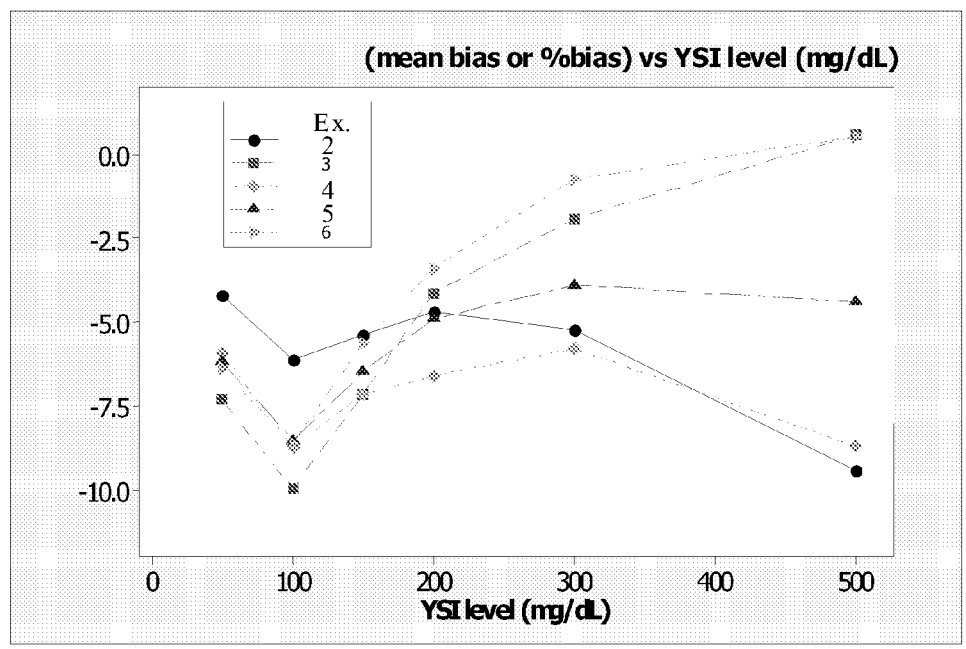
FIG. 2 is a scatterplot graph of bias versus glucose level of the inks of Examples 2 through 6.

Test strips were manufactured using the enzyme ink in accordance with the process set forth in the specification hereinabove. The strips were calibrated by randomly selecting 1500 strips. Blood from 12 different donors was spiked to each of 6 levels (50, 100, 150, 200, 300 and 500 mg) of glucose and 8 strips were given blood from identical donors and levels so that a total of 12×6×8 or 576 tests were conducted for each test batch. These were benchmarked against actual blood glucose concentration by measuring these using a standard laboratory analyzer, a Yellow Springs instrument 2300 ("YSI"). A graph of measured glucose concentration was plotted against actual glucose concentration (or measured current versus YSI current) and a formula $y=mx+c$ least squares fitted to the graph to give a value for batch slope m and batch intercept c. In addition, the bias (50 mg level) and percent bias (100-500 mg levels) were calculated for each glucose level along with the Delta_150 for the ink mixture of each example. The bias, percent bias and Delta_150 are all shown in Table 2 below. A scattperplot of bias or percent bias versus glucose level is shown in FIG. 2.

TABLE 2

| | Mean Bias (50 mg) % bias (100-500 mg) | | | | | | |
|---|---|---|---|---|---|---|---|
| Ex. | 50 | 100 | 150 | 200 | 300 | 500 | Delta 150 |
| 2 | −4.2 | −6.1 | −5.4 | −4.7 | −5.2 | −9.4 | −4.1 |
| 3 | −7.3 | −10.0 | −7.2 | −4.2 | −1.9 | 0.6 | 7.7 |
| 4 | −5.9 | −8.8 | −7.2 | −6.6 | −5.8 | −8.7 | −1.6 |
| 5 | −6.2 | −8.5 | −6.5 | −4.9 | −3.9 | −4.4 | 2.1 |
| 6 | −6.4 | −8.6 | −5.6 | −3.4 | −0.8 | 0.5 | 6.2 |

Figure 3:
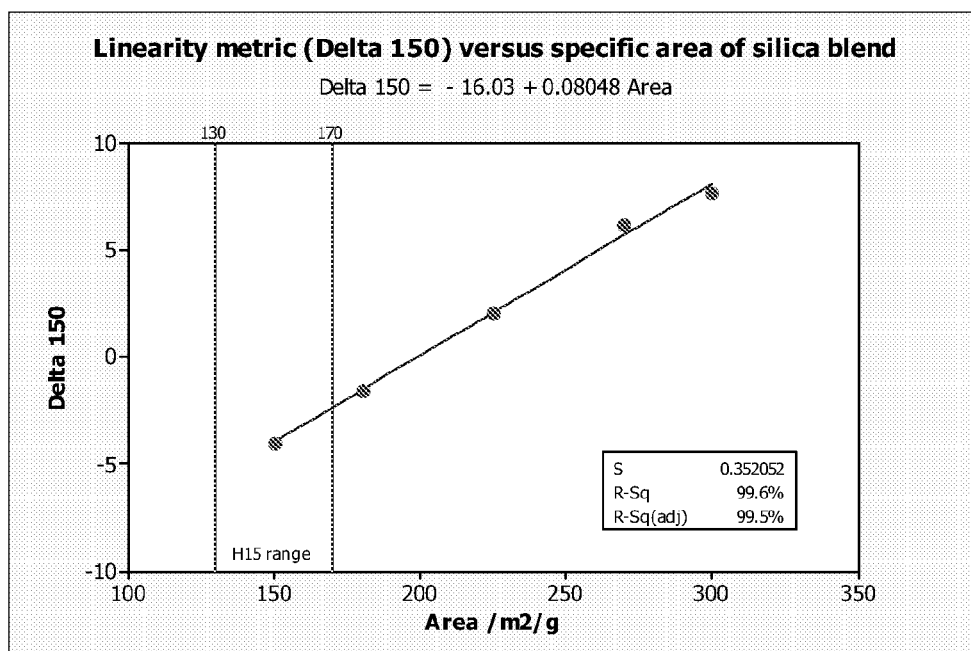
FIG. 3 is a graph of Delta_150 values versus surface area for the inks of Examples 2 through 6.

The results demonstrate that enzyme inks with higher levels of H30 fumed silica produced higher glucose readings at 500 mg/dl producing a small bias value. Inks with little or no H30 had lower glucose readings at 500 mg/dl. A graph of Delta_150 plotted against the normal effective area of the fumed silica achieved by the H30-H15 blend as prepared and the resultant regression is shown in FIG. 3.

Figure 4:
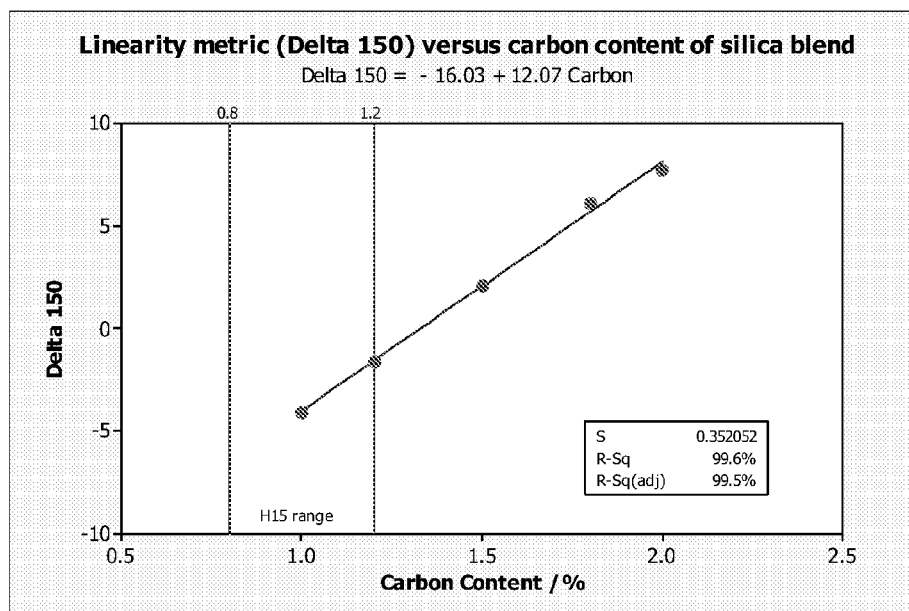
FIG. 4 is a graph of Delta_150 values versus carbon content for the inks of Examples 2 through 6.

A strong correlation between Delta_150 and the specific area is shown. A graph of Delta_150 plotted against the percent carbon content of each grade (H30 and H15) assuming the grades contained the nominal amount of carbon for that grade and the resultant regression is shown in FIG. 4. The same high R-squared value of 99.6% indicates a strong correlation between Delta_150 and the carbon content.

What is claimed is:

1. An enzyme ink composition, comprising an enzyme capable of selectively recognizing glucose in a blood sample, a mediator, and a first and a second fumed silica, wherein the first fumed silica comprises a BET measured surface area of about 130 to 170 $m^2/g$ and a carbon content of about 0.8 to about 1.23 weight percent and the second fumed silica comprises a BET measured surface area of about 270 to 330 $m^2/g$ and a carbon content of about 1.4 to about 2.6 weight percent.

2. The enzyme ink of claim 1, wherein the first fumed silica is present in an amount of about 99 to about 1 weight percent of the total amount of the fumed silicas and the second fumed silica is present in amount of about 1 to about 99 weight percent.

3. The enzyme ink of claim 1, wherein the first fumed silica is present in an amount of about 75 to about 45 weight percent of the total amount of the fumed silicas and the second fumed silica is present in amount of about 25 to about 55 weight percent.

4. The enzyme ink of claim 1, wherein the enzyme is elected from the group consisting of glucose oxidase, glucose dehydrogenase, glucose dehydrogenase with a pyrrolo-quinolone co-factor, and glucose dehydrogenase with a flavin adenine dinucleotide co-factor and the mediator is selected from the group consisting of ferricyanide and ruthenium hexamine trichloride.

5. The enzyme ink of claim 1, wherein the enzyme is glucose oxidase mediator is ferricyanide.

6. An enzyme ink, comprising about 0.3 percent by mass of an antifoam compound, about 0.6 percent by mass of polyvinyl alcohol, about 0.6 percent by mass citric acid, about 1.9 percent by mass trisodium citrate, about 0.6 percent by mass polyvinylpyrrolidone-vinyl acetate copolymer, about 3.27 percent by mass hydroxyethyl cellulose, about 3.6 percent by mass of a first fumed silica with a BET measured surface area of about 130 to 170 $m^2/g$ and a carbon content of about 0.8 to about 1.23 weight percent, about 1.3 percent by mass of a second fumed silica with a BET measured surface area of about 270 to 330 $m^2/g$ and a carbon content of about 1.4 to about 2.6 weight percent, about 0.03 percent by mass potassium hexacyanoferrate III, about 23 percent by mass of potassium ferricyanide; about 2.1 percent by mass glucose oxidase and about 62.4 percent by mass water.

7. A test strip comprising at least two co-planar electrodes, wherein at least one of the electrodes comprises an enzyme ink composition comprising an enzyme capable of selectively recognizing glucose in a blood sample, a mediator, and a first and a second fumed silica, wherein the first fumed silica comprises a BET measured surface area of about 130 to 170 $m^2/g$ and a carbon content of about 0.8 to about 1.23 weight percent and the second fumed silica comprises a BET measured surface area of about 270 to 330 $m^2/g$ and a carbon content of about 1.4 to about 2.6 weight percent.

8. The test strip of claim 7, wherein the first fumed silica is present in an amount of about 99 to about 1 weight percent of the total amount of the fumed silicas and the second fumed silica is present in amount of about 1 to about 99 weight percent.

9. The test strip of claim 7, wherein the first fumed silica is present in an amount of about 75 to about 45 weight percent of the total amount of the fumed silicas and the second fumed silica is present in amount of about 25 to about 55 weight percent.

10. The test strip of claim 7, wherein the enzyme is elected from the group consisting of glucose oxidase, glucose dehydrogenase, glucose dehydrogenase with a pyrrolo-quinolone co-factor, and glucose dehydrogenase with a flavin adenine dinucleotide co-factor and the mediator is selected from the group consisting of ferricyanide and ruthenium hexamine trichloride.

11. The test strip of claim 7, wherein the enzyme is glucose oxidase mediator is ferricyanide.

12. The test strip of claim 7, wherein the enzyme ink comprises about 0.3 percent by mass of an antifoam compound, about 0.6 percent by mass of polyvinyl alcohol, about 0.6 percent by mass citric acid, about 1.9 percent by mass trisodium citrate, about 0.6 percent by mass polyvinylpyrrolidone-vinyl acetate copolymer, about 3.27 percent by mass hydroxyethyl cellulose, about 3.6 percent by mass of a first fumed silica with a BET measured surface area of about 130 to 170 $m^2/g$ and a carbon content of about 0.8 to about 1.23 weight percent, about 1.3 percent by mass of a second fumed silica with a BET measured surface area of about 270 to 330 $m^2/g$ and a carbon content of about 1.4 to about 2.6 weight percent, about 0.03 percent by mass potassium hexacyanoferrate III, about 23 percent by mass of potassium ferricyanide; about 2.1 percent by mass glucose oxidase and about 62.4 percent by mass water.

* * * * *